US006465436B2

(12) United States Patent
Lukas et al.

(10) Patent No.: US 6,465,436 B2
(45) Date of Patent: Oct. 15, 2002

(54) METHOD FOR TREATING ALCOHOL INTOXICATION AND ALCOHOL ABUSE

(75) Inventors: Scott Lukas, Boxborough; David Lee, Cambridge, both of MA (US)

(73) Assignee: McLean Hospital, Belmont, MA (US)

( * ) Notice: Subject to any disclaimer, the term of this patent is extended or adjusted under 35 U.S.C. 154(b) by 0 days.

(21) Appl. No.: 09/871,760

(22) Filed: May 31, 2001

(65) Prior Publication Data

US 2002/0022634 A1 Feb. 21, 2002

Related U.S. Application Data

(60) Provisional application No. 60/208,618, filed on Jun. 1, 2000.

(51) Int. Cl.[7] .............................................. A61K 31/70
(52) U.S. Cl. ......................................... 514/27; 514/456
(58) Field of Search .................................. 514/27, 456

(56) References Cited

U.S. PATENT DOCUMENTS

| | | | |
|---|---|---|---|
| 5,204,369 A | | 4/1993 | Vallee et al. |
| 5,547,671 A | * | 8/1996 | Duthinh .................. 424/195.1 |
| 5,624,910 A | | 4/1997 | Vallee et al. |
| 5,783,189 A | * | 7/1998 | Pei et al. ................. 424/195.1 |
| 5,886,028 A | | 3/1999 | Vallee et al. |
| 6,121,010 A | | 9/2000 | Vallee et al. |
| 6,255,497 B1 | * | 7/2001 | Vallee et al. ................. 549/403 |

OTHER PUBLICATIONS

Lin et al (I), Am. J. Clin. Nurt., vol. 68, pp. 1512S–5s. 1998.*
Keung et al, Proc. Natl. Acad. Sci. USA, vol. 93, pp. 4284–4288, Apr. 1996.*
Lin et al (II), Alcohol Clin. Exp. Res, vol. 20, #4, pp. 659–663 (abstract), Jun. 1996.*
Keung and Vallee, "Daidzin and Daidzein Suppress Free–Choice Ethanol Intake by Syrian Golden Hamsters," *Proc. Natl. Acad. Sci. USA* 90:10008–10012 (1993).
Keung and Vallee, "Therapeutic Lessons from Traditional Oriental Medicine to Contemporary Occidental Pharmacology," *EXS* 71:371–381 (1994).
Keung et al., "Daidzin Suppresses Ethanol Consumption by Syrian Golden Hamsters without Blocking Acetaldehyde Metabolism," *Proc. Natl. Acad. Sci. USA* 92:8990–8993 (1995).
Keung et al., "Potentiation of the Bioavailability of Daidzin by an Extract of *Radix Puerariae*," *Proc. Natl. Acad. Sci. USA* 93:4284–4288 (1996).
Keung et al., "Daidzin Inhibits Mitochondrial Aldehyde Dehydrogenase and Suppresses Ethanol Intake of Syrian Golden Hamsters," *Proc. Natl. Acad. Sci. USA* 94:1675–1679 (1997).
Keung and Vallee, "Daidzin and its Antidipsotropic Analogs Inhibit Serotonin and Dopamine Metabolism in Isolated Mitochondria," *Proc. Natl. Acad. Sci. USA* 95:2198–2203 (1998).
Keung and Vallee, "Kudzu Root: An Ancient Chinese Source of Modern Antidipsotropic Agents," *Phytochemistry* 47:499–506 (1998).
"Kudzu Extract Shows Potential for Moderating Alcohol Abuse," *Am. J. Hosp. Pharm.* 51:750 (1994).
Overstreet et al., "Suppression of Alcohol Intake After Administration of Chinese Herbal Medicine, NPI–028, and its Derivatives," *Alcohol. Clin. Exp. Res.* 20:221–227 (1996).
Rezvani et al., "Chinese Herbal Medicine NPI–028 Reduces Alcohol Intake without Inducing Taste Aversion," *Alcohol. Clin. Exp. Res.* 19:15A (Abstract) (1995).
Shebak and Rindone, "A Pilot Study Exploring the Effect of Kudzu Root on the Drinking Habits of Patients with Chronic Alcoholism," *J. Altern. Complement. Med.* 6:45–48 (2000).
Xie et al., "Daidzin, an Antioxidant Isoflavonoid, Decreases Blood Alcohol Levels and Shortens Sleep Time Induced by Ethanol Intoxication," *Alcohol. Clin. Exp. Res.* 18:1443–1447 (1994).

* cited by examiner

Primary Examiner—James H. Reamer
(74) Attorney, Agent, or Firm—Clark & Elbing LLP

(57) ABSTRACT

Treatment for alcohol dependence or intoxication that involves administering a pharmaceutical composition containing an extract of the kudzu plant, *Pueraria lobata*.

6 Claims, 4 Drawing Sheets

HPLC Trace of Isoflavone Extract of Kudzu

FIG. 1  HPLC Trace of Isoflavone Extract of Kudzu

METHOD FOR TREATING ALCOHOL INTOXICATION AND ALCOHOL ABUSE

CROSS-REFERENCE TO RELATED APPLICATION

This application claims benefit of U.S. provisional patent application Ser. No. 60/208,618, filed on Jun. 1, 2000.

BACKGROUND OF THE INVENTION

The present invention relates to methods of treating alcohol intoxication and alcohol abuse with an extract from the Kudzu plant, *Puararia lobata*.

Ethyl alcohol is the most widely used psychoactive drug in the world. Alcohol abuse and alcohol related diseases represent a serious threat to human health and pose major medical, social, and economic problems. In the United States alone, an estimated 10% of the population is affected by alcoholism. The problems associated with alcohol abuse are very costly, both to the individuals affected and to society at large. The physical, social and psychological harm which can result from alcohol abuse and dependence, such as fetal alcohol syndrome, cirrhosis of the liver, alcohol-related accidental death, homicide, suicide, etc., can be devastating. Thus, there remains a strong need to develop safe and effective therapeutic agents for treating alcohol abuse and dependence.

As public awareness of the problems associated with alcohol abuse has increased in recent years, greater efforts have been devoted to the development of treatments for alcoholism. Much of the current research in this area has focused on methods for treating the effects of alcohol withdrawal through the clinical use of various drugs, such as benzodiazepines and the antidipsotropic agent disulfuram (ANTABUSE™). Recent research has also led to the development of new therapeutic agents which suppress alcohol drinking in humans. For instance, dopamine agonists and antagonists, serotonergic agents, glutamate antagonists, opiate antagonists, ALDH inhibitors, and calcium blockers have been reported to reduce self administration of alcohol in alcoholic humans and alcohol-preferring rats (Banys, 1988; Lawrin et al., 1986; McBride et al., 1989; Naranjo et al., 1990; Rezvani et al., 1990, 1991; Sellers et al., 1992). Also, naltrexone (REVIA™), an opioid receptor antagonist, when combined with psychotherapy, has shown encouraging results in several clinical trials (Berg et al., 1990; O'Malley et al., 1992a,b; Volpicelli et al., 1990, 1992). Unfortunately, many of these current drug treatments are toxic, exhibit low efficacy and patient compliance, have many adverse side effect, and are unsuitable for use with adolescents and pregnant women. Thus, despite these recent advancements, developing effective treatments for alcohol dependence remains a challenging goal.

Since ancient times, Chinese herbalists have known of the medicinal value of the Kudzu plant, *Pueraria lobata*. Radix Puerariae (RP), a related herb in the same family, has long been used in traditional Chinese medicine as a treatment for alcohol intoxication. Although it has been a part of Chinese medicine for over 2000 years, only recently have attempts been made to purify, identify, and classify the active ingredients of RP. Research has shown that RP is a complex mixture having a multitude of components, not all of which have been identified. In addition to starch, some of the major constituents of RP include puerarin, daidzein, daidzin, genistein, 6,7-dimethoxycoumarin, formononetin, β-sitosterol, allantoin, and 5-methylhydantoin.

Recently, Keung and Vallee demonstrated that daidzin and daidzein were the active herbal components isolated from RP that suppressed alcohol intake in Syrian Golden hamsters (Keung and Vallee, 1993a; 1993b; Keung et al., 1995). Daidzein also decreases blood alcohol levels and shortens sleep time induced by alcohol (Xie et al., 1994). Daidzin and daidzein are potent human ALDH-1 inhibitors (Keung et al., 1993a,b), and in U.S. Pat. No. 5,204,369, Vallee et al disclose the use of daidzin as a selective inhibitor of ALDH-1 for the treatment of alcohol dependence.

U.S. Pat. No. 5,783,189 reports that comprehensive fractionation studies on *Pueraria lobata* yielded five isoflavonoids which are primarily responsible for the alcohol consumption suppressing activity of herbal medicines derived from *Pueraria lobata*. Daidzin and daidzein were among the five, as well as puerarin, 3'-methoxypuerarin, and mirificin.

SUMMARY OF THE INVENTION

The invention features pharmaceutical compositions for treating alcohol dependence and intoxication which contains a kudzu extract that includes, by weight, (i) 20–40% puerarin; (ii) 3–10% daidzein; and (iii) 1–5% daidzin, in a pharmaceutically acceptable carrier. Preferably, the composition contains, by weight, 25% puerarin, 5% daidzein and 2.5% daidzin. The pharmaceutical compositions of the invention are preferably adapted for oral ingestion.

These pharmaceutical compositions are useful for the treatment of alcohol dependence and alcohol intoxication. The methods and compositions of the invention are nontoxic, very efficacious, present few, if any, side effects, and can be safely used with pregnant women and adolescents.

Other features and advantages of the invention will be apparent from the following detailed description of the preferred embodiments thereof and from the claims.

DETAILED DESCRIPTION OF THE INVENTION

Figure 1:
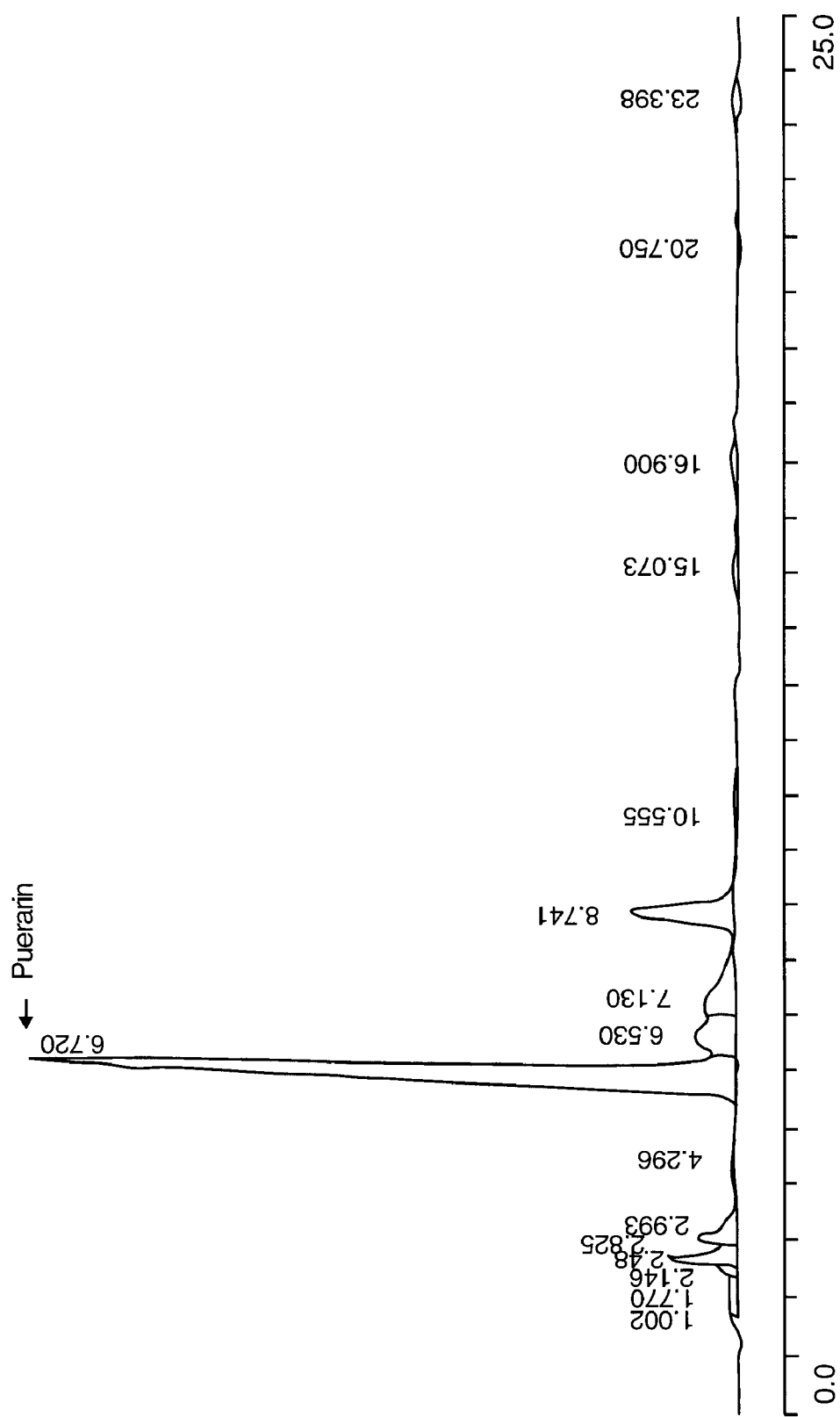
FIG. 1 is a sample HPLC trace of Kudzu extract.

The present invention features a pharmaceutical composition that includes an extract of *Pueraria lobata* (Kudzu). This pharmaceutical composition is useful in the treatment of alcohol dependence and alcohol intoxication, as well as other alcohol-related disorders.

The Kudzu extract of the invention has been shown to reduce the desire of heavy drinkers to consume alcohol and increase their desire to avoid it. The reduction in alcohol consumption that results from the administration of Kudzu is due, at least in part, to the presence of certain isoflavones that occur naturally in the Kudzu plant. A total of at least seven isoflavonoids have been isolated from *Pueraria lobata*, including puerarin, daidzin, daidzein, 3'-methoxy puerarin, and genistein.

The Kudzu plant is ubiquitous in the environment, making it a widely available and easy to obtain. This makes it a highly desirable choice as an aid to control drinking as compared to other currently available treatments. The crude *Pueraria lobata* that is generally available from vendors and wholesale herbal processing plants contains only about 0.61%–0.92% puerarin and 0.10%–0.17% daidzin. Due to this relatively low concentration, it must be given in very high amounts in order to have a substantial therapeutic effect. The present invention provides a Kudzu extract that is very simple and inexpensive to prepare which has an increased concentration of puerarin and other isoflavones, allowing it to be administered in smaller, more manageable doses.

The principal isoflavone component of the invention is puerarin. By containing a relatively high percentage of puerarin, the extract of the invention is superior to other purified isoflavone-containing compositions. Puerarin is coupled to a sugar moiety via a carbon—carbon bond, which is not easily cleaved. This sugar moiety may enhance the solubility of the compound, thereby facilitating its absorption. It is also is believed to be important in drawing the isoflavone across the blood brain barrier via an active transport mechanism. Thus, compounds with a sugar moiety, such as puerarin, as generally more potent than the corresponding aglycone. In contrast, daidzein does not have a sugar moiety and daidzin is coupled to its sugar via a carbon-oxygen bond, which is easily cleaved. Once the sugar is cleaved, daidzin resembles a phytoestrogen that is likely to have estrogenic activity in humans. Thus, the potential risk of unwanted hormonal activity is much less with the present invention as compared to those products which contain significantly higher amounts of daidzin. Although puerarin has been reported to be slightly less active than daidzin in suppressing alcohol intake, puerarin is not an ALDH inhibitor nor a phytoestrogen, and therefore, it is a safer compound with a better therapeutic index than daidzin or daidzein.

Since puerarin cannot be easily synthesized (a method of preparation of puerarin and its analogs in described by Pei et al, U.S. Pat. No. 5,783,189), it is preferably extracted from the raw root product. The pharmaceutical composition of the present invention includes a Kudzu extract that contains about 20–40% puerarin, about 2–10% daidzin, and about 1–5% daidzein. In addition, the extract generally contains about 5% 3-methoxy puerarin. The exact percentages of these isoflavones may vary somewhat depending upon the exact source of the raw Kudzu plant. In a preferred embodiment, the composition contains about 20–30% puerarin, about 3–5% daidzein, and 1–3% daidzin. In a particularly preferred embodiment, the composition contains about 25% puerarin, about 4% daidzein, and about 2.5% daidzin.

The Kudzu extract of the invention is administered systemically, e.g. orally or by IM or IV injection, in admixture with a pharmaceutically acceptable carrier adapted for the route of administration. Oral administration is the preferred route, and therefore the extract is preferably admixed with an orally ingestible carrier (e.g. gelatin) and the composition in preferably in the form of a capsule, tablet, pill, or powder.

Compositions intended for oral use may be prepared according to any method known to the art for the manufacture of pharmaceutical compositions. The compositions may optionally contain sweetening agents, flavoring agents, coloring agents, and preserving agents in order to provide a more palatable preparation. Generally tablets and/or capsules contain active ingredient admixed with non-toxic pharmaceutically acceptable excipients. These excipients may include, for example, inert diluents, such as calcium carbonate, sodium carbonate, lactose, calcium phosphate, sodium phosphate, or kaolin. Binding agents and/or lubricating agents may also be used. In one preferred embodiment the capsules also contain soy. For soft gelatin capsules, the active ingredient is mixed with water or an oil medium.

Dosage levels on the order of about 0.1 mg to about 140 mg per kilogram of body weight per day (from about 1.0 mg to about 10.0 g per 70 kg patient per day) are useful in the treatment of the above mentioned alcohol-related conditions. The amount of active ingredient that may be combined with the carrier materials to produce a single dosage will vary depending upon the subject being treated and the particular mode of administration. A variety of physiologically acceptable carriers can be used in the present invention and their formulations are known to one skilled in the art and are described, for example, in *Remington's Pharmaceutical Sciences,* ($18^{th}$ edition), ed. A. Gennaro, 1990, Mack Publishing Company, Easton, Pa. and Pollock et al.

The individual doses or capsules preferably contain anywhere between 400–500 mg up to about 1 g of Kudzu extract. Preferably, patients take two to three capsules, three times per day (e.g., once in the morning, once in the early afternoon, and again in the evening). In general, the desired daily dosage should be taken for a prolonged period, usually at least one week, preferably two to six weeks, although longer periods of administration of a month or more may be needed.

One skilled in the art will appreciate that the exact individual dosages may be adjusted somewhat depending upon a variety of factors, including the exact amounts of isoflavones present in the extract, the time of administration, the route of administration, the rate of excretion, and the age, weight, health, and gender of the patient. In addition, the severity of the alcohol-related problem being treated will also have an impact on the dosage level. Similarly, the dose level for suppressing an urge for alcohol may vary among individuals depending upon the severity of the individual's symptoms and/or the individual's predisposition or susceptibility to alcoholism or alcohol abuse. The optimum dosage can generally be determined by monitoring the amount of alcohol consumed by the individual while on the medication or by the intensity of the individual's desire for alcohol.

Preparation of Kudzu Extract

Crude *Pueraria lobata* is commercially available and may be obtained from an herbal medicine supplier. The identity of the plant should be verified by a trained botanist prior to extraction. An accurate botanical identification of the herbal plant starting materials is essential for large scale preparation and clinical use.

In order to prepare the isoflavone extract of the invention, the crude dry root of *Pueraria lobata* was first ground in a grinder to obtain a powder. This may be done using a domestic food processor or similar type device. The powder of Kudzu root (10 kg) was then suspended in a 95% ethanol (50 L) for 24 hours. The suspension was then filtered, using either a cotton cloth or paper filter, and filtrate was concentrated using a rotary evaporator under reduced pressure to give the crude Kudzu residue.

The crude residue was loaded onto an aluminum oxide ($Al_2O_3$) column and eluted with a combination of water and methanol. The column is eluted starting with a 10%/90% water/methanol combination. The concentration of methanol is gradually increased by increments of about 2%, until the final elution is with 100% methanol.

The eluted fractions were identified using HPLC (reverse phase; C-18 column). The concentration of isoflavones ranged from about 10–90% in the eluted fractions. All fractions containing isoflavones were then combined and concentrated using a rotary evaporator under reduced pressure to produce an isoflavone extract as a yellowish powder. A representative HPLC profile of the combined extract is shown in FIG. 1. Testing of the powder with HPLC has determined that the isoflavone extract contained about 25% puerarin (±5%) and about 5% (±3%) other isoflavones, including 3'-methoxy-puerarin, daidzin, and daidzein.

The present invention is illustrated by the following examples, which are in no way intended to be limiting of the invention.

Example 1

Effectiveness of Kudzu Extract in Reducing the Desire to Use Alcohol in Heavy Drinkers A group of heavy drinkers, i.e., those who scored between 2–6 on the Cahalan Quantity Frequency Volume (CQFV) scale, were tested to determine the effectiveness of Kudzu extract on the desire to use alcohol. The subjects were given capsules containing Kudzu extract, raw Kuzdu root, or a placebo. The Kudzu extract capsules were 600 mg capsules which contained about 500 mg of Kudzu extract having a concentration of about 25% puerarin, and about 1–7% of daidzin and daidzein. The dosing schedule was 3capsules t.i.d. for 5 days, followed by a visit to the laboratory on the sixth day for an alcohol challenge (0.7 g/kg).

Figure 2:
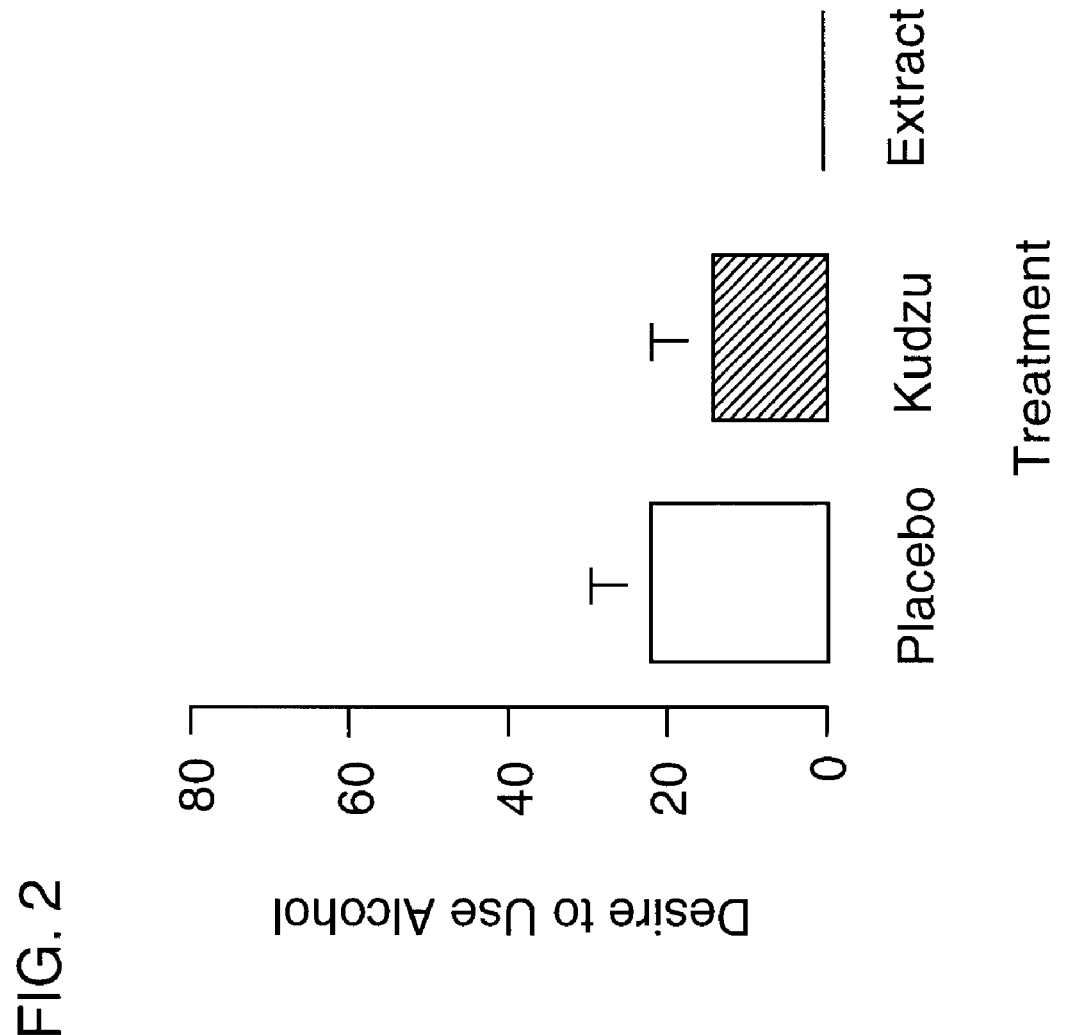
FIG. 2 is bar graph that compares the desire to use alcohol among heavy drinkers who were treated with either raw Kudzu root, Kudzu extract, or a placebo.
Figure 3:
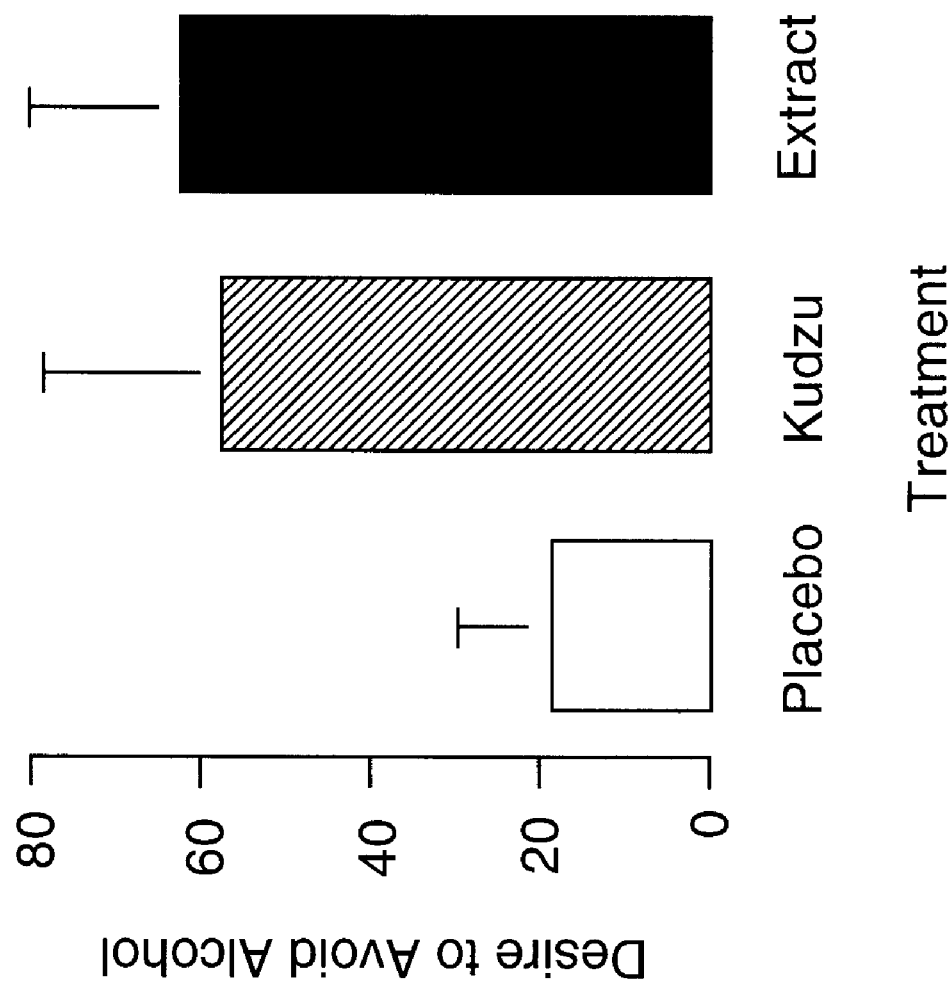
FIG. 3 is a bar graph that compares the desire to avoid alcohol among heavy drinkers who were treated with either raw Kudzu root, Kudzu extract, or a placebo.

The participants were asked to rate their desire to use alcohol, as well as their desire to avoid alcohol, on a scale of 1–100 using a Visual Analog Scale (VAS). The results of the questionnaires are shown in FIGS. 2 and 3. The graphs demonstrates that, compared to placebo and raw kudzu root, the extract appears to significantly reduce the desire to drink among heavy drinkers. The subjects desire to use alcohol after five days of treatment was zero when they were treated with Kudzu extract. Conversely, their desire to avoid alcohol was compared to the placebo. These results strongly suggest that the Kudzu extract is effective at treating alcohol dependence and abuse, and is more potent than crude Kudzu.

Example 2

Effectiveness of Kudzu Extract in Reducing Alcohol Intake in Light to Moderate Drinkers A naturalistic study was conducted using college age women (average age 23 years old) who were light to moderate social drinkers who typically binge drank on weekends. However, they did tend to have 1–2 drinks every day, on average. Subjects wore a wrist actigraphy device which monitored their sleep awake activity and also allowed them to record the number of drinks that they consumed by pressing a button; these data were all time- and date-coded. Subjects returned to the laboratory twice a week for urine tests (to confirm compliance with the medication) and to collect breath samples for alcohol. Weekly blood tests were performed to ensure safety.

Figure 4:
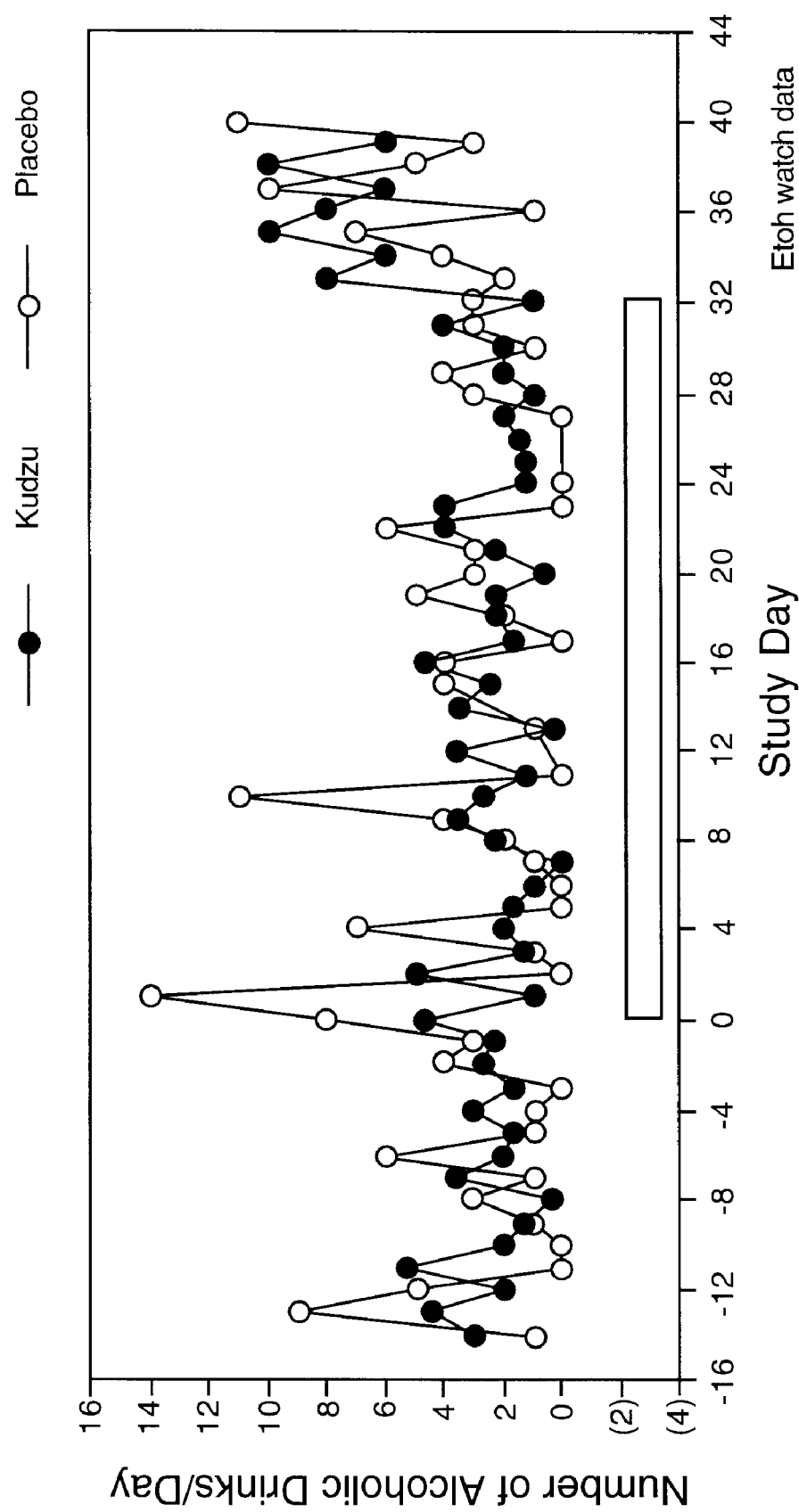
FIG. 4 is profile that compares the daily drinking behavior of light to moderate social drinkers who were treated with either Kudzu extract or a placebo.

Subjects wore the device for two weeks in order to obtain a baseline of their drinking behavior. At that point, they were given packets of capsules and told to take two in the morning and two again at night (approximately 9 am and 9 pm) for 0–32 days (FIG. 4; as indicated by the bar). Follow-up studies were conducted for another two weeks. Packets contained either kudzu extract (as described in Example 1) or placebo (gelatin). Medications were given on a double-blind basis and the dosing was determined randomly.

Subjects were instructed to engage in their usual daily activities and to record the number of drinks that they consumed, 24 hours a day, 7 days a week. Compliance was excellent as all urine screens tested positive for the vitamin marker that was placed in the capsules. Subjects reported no side effects at all and were unable to detect any effects of the active (or placebo) medication. All blood and urine tests were normal.

FIG. 4 shows the effects of kudzu treatment on drinking behavior. While the daily averages did not change significantly, two of the three kudzu-treated subjects had 6–7 zero drinking days during the first two weeks of treatment. The third subject had two days of very heavy drinking which were later discovered to be due to her attending a wedding (days 1 and 3 of the treatment phase). The placebo-treated subject continued to drink as usual and had a number of "binges" during the treatment phase. During the baseline phase all three kudzu treated subjects had episodes of binge drinking whereas, only one subject in the kudzu-treated group experienced a binge episode during treatment. Interestingly, the number of daily drinks increased for both treatment groups when the double-blind medication was stopped (on day 32).

These data suggest that light to moderate daily social drinkers who take kudzu extract may find that their urge to drink excessively is curbed and will likely experience a reduction in "binge" drinking. The reduction in binge episodes is significant as this behavior often heralds the onset of more serious drinking problems. Thus, while kudzu extract may not fully eliminate drinking behavior (although the kudzu-treated subjects had many zero-drinking days), it appears to be an effective adjunct treatment to ongoing psychotherapy because it may increase the number of "sober" days per week, reduce the number of binge drinking episodes, and has no significant side effects.

Other Embodiments

From the above description, one skilled in the art can easily ascertain the essential characteristics of the present invention, and without departing from the spirit and scope thereof, can make various changes and modifications of the invention to adapt it to various usages and conditions. All publications, patents, and patent applications mentioned in this specification are incorporated by reference.

What is claimed is:

1. A method for treating alcohol dependence or intoxication in a human patient, comprising administering to a patient a pharmaceutical composition comprising, by weight, (i) 20–40% puerarin; (ii) 3–10% daidzein; and (iii) 1–5% daidzin.

2. The method of claim 1, wherein the composition comprises, by weight, 25% puerarin; 5% daidzein; and 2.5% daidzin.

3. The method of claim 1 or 2, wherein the composition is administered orally.

4. A pharmaceutical composition for treating alcohol dependence or intoxication comprising, by weight, (i) 20–40% puerarin; (ii) 3–10% daidzein; and (iii) 2–5% daidzin, in a pharmaceutically acceptable carrier.

5. The composition of claim 4, wherein the composition comprises, by weight, 25% puerarin; 5% daidzein; and 2.5% daidzin.

6. The composition of claim 4 or 5, wherein the composition is adapted for oral ingestion.

* * * * *

UNITED STATES PATENT AND TRADEMARK OFFICE
CERTIFICATE OF CORRECTION

PATENT NO. : 6,465,436 B2  Page 1 of 1
APPLICATION NO. : 09/871760
DATED : October 15, 2002
INVENTOR(S) : Scott Lukas and David Lee It is certified that error appears in the above-identified patent and that said Letters Patent is hereby corrected as shown below:

Column 1, line 8 following the CROSS REFERENCE TO RELATED APPLICATION section, please insert the following paragraph:

--STATEMENT REGARDING FEDERALLY SPONSORED RESEARCH

This invention was made with government support under federal funds awarded by NIH grant, AA010536. The government has certain rights in the invention.--

Signed and Sealed this

Twenty-seventh Day of April, 2010

David J. Kappos
*Director of the United States Patent and Trademark Office*